United States Patent
Henry et al.

(10) Patent No.: US 6,889,080 B2
(45) Date of Patent: May 3, 2005

(54) DISCRIMINATION OF ATRIAL FIBRILLATIONS FOR AN ACTIVE IMPLANTABLE MEDICAL DEVICE, IN PARTICULAR A DEFIBRILLATOR/CARDIOVERTOR

(75) Inventors: Christine Henry, Paris (FR); Marcel Limousin, Paris (FR)

(73) Assignee: ELA Medical S.A., Montrouge (FR)

( * ) Notice: Subject to any disclaimer, the term of this patent is extended or adjusted under 35 U.S.C. 154(b) by 328 days.

(21) Appl. No.: 09/994,978

(22) Filed: Nov. 27, 2001

(65) Prior Publication Data

US 2002/0169483 A1 Nov. 14, 2002

(30) Foreign Application Priority Data

Nov. 27, 2000 (FR) .............................. 00 15293

(51) Int. Cl.[7] ................ A61N 1/365; A61N 1/39
(52) U.S. Cl. ................ 607/14; 607/5; 600/518
(58) Field of Search .................. 607/4–9, 27–29, 607/14; 600/515, 518

(56) References Cited

U.S. PATENT DOCUMENTS

| | | | |
|---|---|---|---|
| 5,107,850 A | | 4/1992 | Olive .......................... 128/705 |
| 5,267,559 A | * | 12/1993 | Jin et al. ........................ 607/5 |
| 5,350,406 A | | 9/1994 | Nitzsche et al. ............... 607/14 |
| 5,366,486 A | * | 11/1994 | Zipes et al. ..................... 607/5 |
| 5,462,060 A | * | 10/1995 | Jacobson et al. ............. 600/515 |
| 5,486,199 A | * | 1/1996 | Kim et al. ...................... 607/5 |
| 5,620,471 A | * | 4/1997 | Duncan ........................ 607/14 |
| 5,814,081 A | * | 9/1998 | Ayers et al. .................... 607/5 |
| 5,868,793 A | | 2/1999 | Nitzsche et al. ................ 607/5 |
| 6,041,251 A | * | 3/2000 | Kim et al. .................... 600/518 |
| 6,047,210 A | * | 4/2000 | Kim et al. ...................... 607/4 |
| 6,047,213 A | * | 4/2000 | Sirokman et al. ............... 607/9 |
| 6,178,350 B1 | * | 1/2001 | Olson et al. .................... 607/4 |

FOREIGN PATENT DOCUMENTS

EP 0 879 621 A 11/1998 .......... A61N/1/368

* cited by examiner

Primary Examiner—Jeffrey R. Jastrzab
(74) Attorney, Agent, or Firm—Orrick Herrington & Sutcliffe, LLP

(57) ABSTRACT

An active implantable medical device, in particular a defibrillator/cardioverter, with a sophisticated discrimination of atrial fibrillations. This device is able to deliver therapy for defibrillation, cardioversion, and/or ventricular and/or atrial antitachycardiac pacing stimulation; sense the ventricular and atrial activity; identify a suspicion of and confirm the presence of episodes of tachycardia in the activity thus sensed; analyze the stability of detected RR intervals and the stability of the associated PR intervals; and, in the event of a detection of stable RR intervals and unstable PR intervals, discriminate between atrial fibrillation with fast ventricular rhythm and atrial fibrillation with ventricular tachycardia, and to control delivery of a differentiated therapy according to one case or the other. A bi-tachycardia discrimination also can be made.

9 Claims, 1 Drawing Sheet

Figure 1:
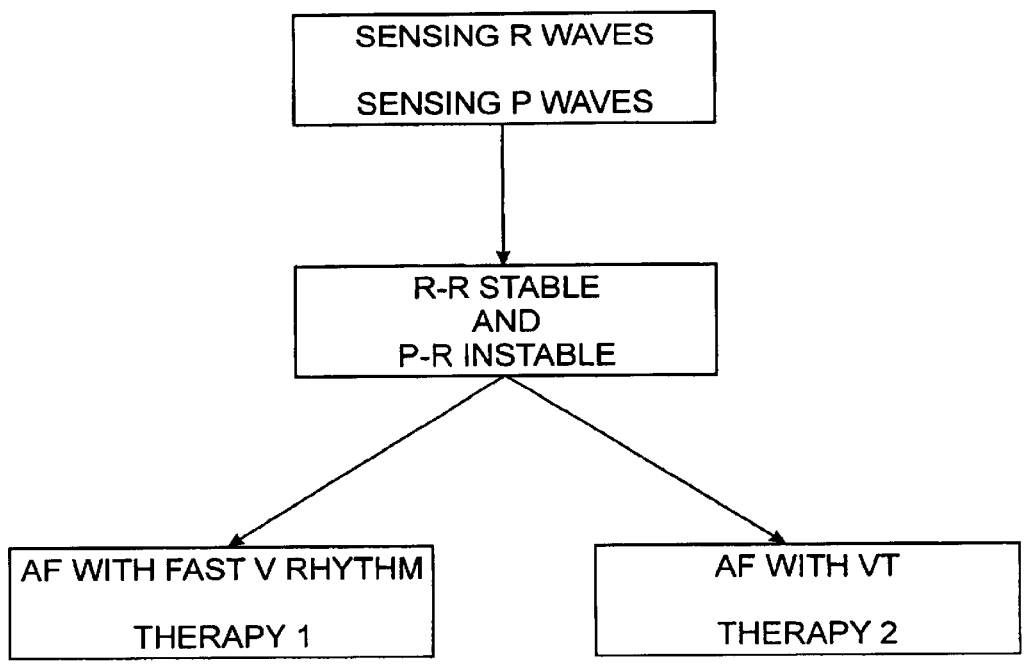

DISCRIMINATION OF ATRIAL FIBRILLATIONS FOR AN ACTIVE IMPLANTABLE MEDICAL DEVICE, IN PARTICULAR A DEFIBRILLATOR/CARDIOVERTOR

FIELD OF THE INVENTION

The present invention is directed to "active implantable medical devices" as such devices are defined by the Jun. 20, 1990 directive 90/385/CEE of the Council of the European Communities, and more particularly to the family of devices that are able to deliver to the heart pulses of high energy (i.e., an energy level notably exceeding the energy level provided for conventional pacing stimulation) in order to terminate a tachyarrythmia. Such devices also typically include a programmed therapy mode of stimulation at high frequency or Anti-Tachycardia Pacing ("ATP"). These devices are commonly called "implantable defibrillators" or "implantable cardiovertors". It should, however, be understood that the invention also covers implantable defibrillator/cardiovertor/pacemaker and implantable defibrillator/pacemaker devices.

BACKGROUND OF THE INVENTION

The aforementioned devices include a pulse generator that monitors the patient's cardiac activity and generates high energy stimulation pulses when the heart presents a ventricular arrhythmia that is deemed likely to be treated. When the high energy lies between approximately 0.1 and 10.0 J, the therapy is known as "cardioversion" and the electric stimulation shock delivered is called "a cardioversion shock." When the energy level is greater than approximately 10.0 J, the therapy is called "defibrillation" and the electric shock delivered is called a "defibrillation shock."

The high energy shock must be delivered when a ventricular tachycardia (VT) is detected, provided that the condition detected as a VT condition is indeed a true VT condition, and not a supraventricular tachycardia (SVT) condition (or some other condition). Indeed, in the case of an SVT condition, the tachycardia is of an atrial origin and the therapy shock that would be delivered would be without effect because the electrode that delivers the defibrillation therapy or, if necessary, the stimulation (ATP) therapy, is not located in the atrium. Actually, these situations cover various forms of a heartbeat rate disorder: When in the presence of an abnormally fast heartbeat rate (i.e., a tachyarrhythmia), this disorder can be caused by a ventricular fibrillation (VF), a ventricular tachycardia (VT), a sinusal tachycardia (ST) or a supraventricular tachycardia (SVT). A supraventricular tachycardia disorder condition covers atrial tachycardia, atrial flutter and atrial fibrillation (AF).

Heart beat rate disorders can exist simultaneously, and in such case one speaks about "bi-tachycardia," in particular, for example, the presence of an atrial fibrillation combined with a ventricular tachycardia.

The diagnosis of a tachycardia condition or disorder can be performed, in a way in itself known, starting from criteria such as the ventricular frequency, the stability of the ventricular intervals (RR intervals), the analysis of atrio-ventricular association (revealed by the stability of the PR intervals), and the mode of starting of tachycardia (the presence of an abrupt acceleration in the rate and the cavity of origin, ventricular or atrial). One will be able in particular to refer to the EP-A-0 626 182 and its counterpart U.S. Pat. No. 5,462,060, both commonly assigned to the assignee hereof, Ela Médical, which describes a basic algorithm for the detection and classification of the tachyarhythmia, which U.S. patent is incorporated herein by reference. This algorithm has been implemented in the commercial products sold under the Defender™ and Alto™ brands and available from Ela Médical, Montrouge France.

The EP-A-0 838 235 and its counterpart U.S. Pat No. 5,868,793, and the EP-A-0 813 888 and its counterpart U.S. Pat No. 5,891,170 (both assigned to Ela Medical), describe various improvements of the basic algorithm, making it possible to improve further the discrimination between VT and SVT, in particular to avoid false positive diagnoses, i.e., an indication of a VT whereas it was actually a SVT, or false negative diagnoses, i.e., an indication of an SVT whereas it was actually a VT. The U.S. Pat. Nos. 5,868,793 and 5,891,170 are incorporated herein by reference in their entirety.

OBJECTS AND SUMMARY OF THE INVENTION

The starting point of the present invention lies in the observation by the inventors of certain clinical situations that have arisen in which the aforementioned algorithm nevertheless yields a false diagnosis of VT and thus may result in a risk of applying a sub-optimal or ineffective therapy. It is, therefore, an object of the present invention to minimize the likelihood of producing a false diagnosis of VT and reduce the risks associated with such a situation.

The aforementioned clinical analysis has revealed a need to treat specifically, in the algorithm of tachycardia detection, the case where an atrial fibrillation (AF) is present at the same time as a fast and stable ventricular rhythm. Indeed, the decision tree of the known algorithm is such that, if the ventricular rhythm is at the same time fast (i.e., greater than the VT threshold detection frequency) and stable, and that the PR interval is not stable, i.e., in the absence of an atrio-ventricular association, then the device considers that the patient is in VT.

However, in the case of an arrhythmia having AF and a fast ventricular rhythm, the high frequency of the ventricular rhythm increases the stability, and AF induces an instability of the PR interval. But AF, which is a form of SVT, does not justify application of a ventricular shock therapy, unlike a true VT.

It is thus desirable to improve the algorithm by adding an additional discrimination criterion to make it possible to recognize and treat specifically this disorder situation.

Broadly, the present invention is directed to an improvement of a device of the type described in the aforementioned EP-A-0 626 182 and U.S. Pat. No. 5,462,060, which includes: means for delivering a defibrillation and/or cardioversion therapy and/or atrial and/or ventricular antitachycardic stimulation; means for sensing the ventricular and atrial activity, including P-waves and R-waves; and means for suspecting and for confirming the presence of episodes of tachycardia in the activity thus sensed, including analyzing the stability of detected RR intervals and the stability of the associated PR intervals.

In accordance with the present invention, this device also includes means for discriminating between atrial fibrillation with a fast ventricular rhythm and atrial fibrillation with ventricular tachycardia, and to control a differentiated therapy according to the case discriminated, which means operates in the event of a detection of stable RR intervals and unstable PR intervals In one embodiment, the means for discriminating comprises means for measuring the amplitude of the detected P-waves, means for analyzing the stability of these measured amplitudes, and means for determining a presence of an atrial fibrillation in the event of a determined instability greater than a preselected threshold.

In a second embodiment, the means for discriminating comprises means for temporarily inhibiting the means for sensing the ventricular activity, and means for analyzing the atrial frequency and determining the presence of an atrial fibrillation in the event of an atrial frequency greater than the ventricular frequency.

In a third embodiment, the means for discriminating comprises means for temporarily inhibiting the means for sensing the ventricular activity, means for measuring an atrial capture, and means for determining a presence of an atrial fibrillation in the event of an absence of atrial capture.

In a fourth embodiment, the means for discriminating comprises means for evaluating a conduction delay between the right atrium and the left atrium, means for analyzing the stability of this delay, and means for determining a presence of an atrial fibrillation in the event of a determined instability greater than a preselected threshold.

It should be understood than the means for discriminating can comprise one or more of the aforementioned embodiments in any combination, such that a greater degree of confidence can be obtained with the use of more than one embodiment.

In a more preferred embodiment, very advantageously, the device according to the present invention also comprises means for detecting a bi-tachycardia condition and means for controlling an adapted therapy, said means operating when the means for discriminating detects the presence of an atrial fibrillation. The bi-tachycardia condition detecting means can be:

(1) means for analyzing the duration of RR intervals, to determine the presence of a bi-tachycardia in the event of a detection of at least one cardiac cycle of a duration greater than a given threshold during a series of successive cardiac cycles, and/or (2) means for applying an atrial shock therapy of low energy and evaluating the effectiveness of said applied therapy, to determine the presence of a bi-tachycardia condition in the event of a persistence of atrial fibrillation after said applied therapy, and/or (3) means for temporizing, i.e., interposing a delay before taking any action, to determine the presence of a bi-tachycardia condition in the event of a persistence of atrial fibrillation at the end of the delay.

DETAILED DESCRIPTION OF THE INVENTION

One now will describe in more detail various preferred embodiments of the present invention.

The device in accordance with a preferred embodiment of the present invention uses an algorithm for the detection and classification of tachyarrhythmia of a defibrillator such as the Defender™ or Alto™ model devices available from Ela Médical, which algorithm is improved in the manner that is discussed herein.

The first stage of the analysis concerns isolating a particular case in which: (1) the ventricular rhythm is fast, i.e., greater than a the frequency threshold for diagnosing VT, (2) the ventricular rhythm is stable, based on evaluating an RR interval criterion, and (3) there is no atrio-ventricular association, based on evaluating a stability of the PR intervals criterion.

More preferably, the apparatus described in the aforementioned EP-A-0 626 182 and U.S. Pat. No. 5,464,060 defines that there is stability of the RR intervals when the peak of autocorrelation, divided by the total of autocorrelation, exceeds a given ratio (as noted, the peak of autocorrelation is the maximum number of recent intervals in the ventricle which satisfy a criterion of a predetermined stability). It defines that there is stability of conduction when the value of the peak of intercorrelation, divided either by the value of the peak of autocorrelation, or, in alternative, by the total of intercorrelation, exceeds a given ratio (the peak of intercorrelation is the maximum number of intervals of conduction coming from the atrium which satisfies a predetermined criterion of stability). In other words, in the first above-mentioned case, one compares the stability of conduction between the two cavities with those intervals in the ventricle, while in the second case, one expresses the stability of conduction between the two cavities according to the totality of supposed conductions.

If one is thus in the case of a fast and stable ventricular rhythm and an unstable conduction, one proceeds then, in a manner characteristic of the invention, with a complementary analysis so as to determine if one is in the presence of AF with a VT or of an AF with fast ventricular rhythm. This analysis can be carried out in several different manners which are presented as alternative embodiments. A first technique concerns measuring the amplitude of the P-waves and to evaluate the variations, cycle to cycle, of those amplitudes. If this variability is high, then the algorithm considers that there is presence of AF. The criterion of variability of the amplitude as high can be regarded as verified when, for example, one measures a variation of the level of amplitude greater than 20% for at least two cycles of four successive cycles.

A second technique concerns analyzing the atrial frequency, and considering that one is in the presence of AF if the atrial frequency is greater than the ventricular frequency. More preferably, to allow this evaluation, the device is commutated (i.e., its operating mode is changed) from a dual chamber pacing mode (DDD) to a single chamber pacing mode (AAI) to improve the atrial sensing by minimizing disturbances introduced by the detection of the ventricle. In this regard, it is noted that the analysis of AF can be disturbed by the presence of the atrial absolute refractory period used in dual chamber pacing that can limit the detection of certain P-waves. Once the diagnosis of the fast and stable ventricular rhythm (which thus gives a reference value for the ventricular frequency) is carried out, the apparatus collects and analyzes the atrial frequency, for example, over a duration of from four to five seconds, in a mode of atrial detection only (the AAI mode). An atrial frequency greater than the ventricular reference frequency then reveals the presence of AF. This technique of detection of AF is more particularly adapted if the patient is equipped with a probe for atrial detection having a short dipole, which notably reduces the risk of detection of a ventricular depolarization.

A third technique concerns carrying out a test of atrial capture after stimulation, i.e., the voltage threshold of the stimulation pulse amplitude necessary to cause a depolarization of the cavity to which the pulse is applied. The detection of capture is, for example, operated in the manner described in the EP-A-0 552 357 and its corresponding U.S. Pat. No. 5,411,533, assigned to Ela Médical, the disclosure of which is incorporated herein by reference and to which one skilled in the art may refer. The device, still preferably temporarily commutated to operate in an AAI pacing mode to improve atrial sensing, delivers an atrial stimulation (maximum: 5 V and 1 ms) with a coupling interval that is approximately 200 ms greater than the last detected atrial event, and then the measurement of the evoked potential is carried out. If the means for measuring the capture confirms the existence of an atrial capture, then the device considers that it is in the presence of a true VT; in the contrary case, it considers that it is an AF, because a stimulation of the atrium in the presence of AF rarely produces an atrial capture.

A fourth technique relies on one of the characteristics of AF, namely the variability of the depolarization of the atrium, characterized by a very variable conduction delay between the right atrium and the left atrium. This technique is advantageously employed in a multisite device, where the patient is equipped with a detection probe in the right atrium and a detection probe in the left atrium. Advantageously, these probes are probes having a short dipole to limit the risks of detecting ventricular depolarization. The two atrial probes are respectively connected to distinct detection amplifiers, and measurement of the right/left interval is carried out over several consecutive cycles. Preferably, for this technique, the device is temporarily commutated to operate in the AAI pacing mode to improve atrial sensing. If the measured intervals vary over a broad range, for example, more than 50 ms, then the device considers that it is in the presence of AF.

A further improvement in accordance with the techniques of the present invention described above concerns, when the apparatus determines the presence of AF, performing an additional discrimination to determine if it is a simple AF or a "bi-tachycardia," i.e., of the combination of AF and VT, because these two cases respectively have different corresponding therapies. This additional discrimination can be performed in one of several different manners.

A first technique concerns applying to the patient a therapy that includes a low energy atrial shock (light shock) and thereafter analyzing the heartbeat rate. If the shock terminates the disorder, it was probably a simple AF disorder; on the other hand, the failure of the atrial shock to stop the disorder can confirm the VT, and thus it is necessary to apply a ventricular therapy (eventually ATP) or a strong shock to resolve the VT.

A second technique concerns temporizing, that is, delaying a certain amount of time before taking any action, and then analyzing the heartbeat rate again after the delay to determine whether the disorder disappeared. In this regard, it is known that conducted AF is a disorder that occurs in salvos. Thus, if the AF disorder spontaneously disappeared at the end of the delay, one can conclude that it was probably a simple conducted AF that has ended. On the other hand, if the disorder persists, it can be concluded that there is a VT combined with AF, and the device than delivers a suitable ventricular therapy.

A third technique is based upon the observation that the salvos of a conducted AF are embedded with one or more long cycles. The discrimination of the bi-tachycardia thus can be performed by searching for a long cycle, for example, the search for a cycle of a coupling duration greater than an average of the four last durations measured RR intervals during the episode of tachycardia, which average is increased by an amount such as 63 ms. If such a cycle is found in the last 24 cycles analyzed, the device will consider that there is a presence of AF; in the contrary case, it will consider that there is VT, and therefore a bi-tachycardia condition.

The EP-A-0 813 888 and its corresponding U.S. Pat. No. 5,891,170 assigned to Ela Médical, the disclosure of which is hereby incorporated herein by reference, and to which a person of ordinary skill in the art may refer, describe one such process of searching for a long cycle, in order to temporarily modify the parameters and/or the criteria of classification of an algorithm for analyzing the tachycardia.

It should be understood that the present invention is preferably implemented in software of a microprocessor controlled implantable medical device, to acquire the indicated cardiac activity and process that activity to determine cardiac events. Suitable devices include, but are not limited to the aforementioned Defender™ and Alto™ devices. Advantageously, the present invention can be downloaded to an already implanted device by an external programmer, in a conventional manner, as software instructions to modify the operation of the already implanted device, for such devices that are able to receive software instructions and to modify its operation in response thereto.

One skilled in the art will appreciate that the present invention can be implemented by embodiments other that the particular embodiments disclosed, which are presented for purposes of illustration, and not of limitation.

We claim:

1. An active implantable medical device, in particular a defibrillator/cardiovertor, having:

means for delivering a therapy for treatment of tachycardia including at least one of defibrillation, cardioversion, ventricular antitachycardiac pacing and atrial antitachycardiac pacing, means for sensing the ventricular and atrial activity including R-waves and P-waves, and means for suspecting and confirming a presence of an episode of tachycardia in response to the sensed activity, said means including means for analyzing a stability of RR intervals and a stability of associated PR intervals, wherein the improvement comprises:

means, operating in response to a detection of stable RR intervals and unstable PR intervals, for discriminating between atrial fibrillation with a fast ventricular rhythm and atrial fibrillation with a ventricular tachycardia, and for controlling delivery of a differentiated therapy according to said discrimination.

2. The device of claim 1, wherein the means for discriminating further comprises means for measuring an amplitude of the sensed P-waves, mean for analyzing the stability of said amplitudes, and means for determining the presence of an atrial fibrillation in the event of an instability greater than a preselected threshold.

3. The device of claim 1, wherein the means for discriminating comprises means for temporarily inhibiting the means for sensing the ventricular activity, means for analyzing the atrial frequency, and means for determining a presence of an atrial fibrillation in the event of an atrial frequency greater than the ventricular frequency.

4. The device of claim 1, wherein the means for discriminating further comprises means for temporarily inhibiting the means for sensing ventricular activity, means for determining an atrial capture, and means for determining a presence of an atrial fibrillation in the event of an absence of atrial capture.

5. The device of claim 1, wherein the means for discriminating comprises means for evaluating a conduction delay between the right atrium and the left atrium, means for analyzing the stability of said delay, and means for determining the presence of an atrial fibrillation in the event of an instability greater than a preselected threshold.

6. The device of claim 1, further comprising means for detecting a bi-tachycardia and controlling delivery of an adapted therapy, said bi-tachycardia detecting means operating when the means for discriminating detects the presence of an atrial fibrillation.

7. The device of claim 6, wherein the bi-tachycardia detecting means comprises means for analyzing a duration of RR intervals and determining a presence of a bi-tachycardia in the event of a detection of at least one cycle of a duration greater than a preselected threshold during a series of successive cardiac cycles.

8. The device of claim 6, wherein the bi-tachycardia detecting means comprises means for applying an atrial low energy shock therapy and evaluating the effectiveness of said therapy, and means for determining the presence of a bi-tachycardia in the event of persistence of atrial fibrillation after said therapy.

9. The device of claim 6, wherein bi-tachycardia detecting means comprise means for evaluating the heartbeat rate after a delay and determining the presence of a bi-tachycardia in the event of persistence of atrial fibrillation at the end of said delay.

* * * * *